(12) United States Patent
Chen et al.

(10) Patent No.: US 11,564,956 B2
(45) Date of Patent: Jan. 31, 2023

(54) LACTOBACILLUS PLANTARUM WITH COLORECTAL CANCER INHIBITION FUNCTION AND USE THEREOF

(71) Applicant: Jiangnan University, Wuxi (CN)

(72) Inventors: Wei Chen, Wuxi (CN); Gang Wang, Wuxi (CN); Eryin Wang, Wuxi (CN); Jianxin Zhao, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 69 days.

(21) Appl. No.: 16/771,224

(22) PCT Filed: Jul. 19, 2018

(86) PCT No.: PCT/CN2018/092671
§ 371 (c)(1),
(2) Date: Jun. 10, 2020

(87) PCT Pub. No.: WO2019/085521
PCT Pub. Date: May 9, 2019

(65) Prior Publication Data
US 2022/0096570 A1 Mar. 31, 2022

(30) Foreign Application Priority Data
Nov. 3, 2017 (CN) .......................... 201711068300.3

(51) Int. Cl.
| | |
|---|---|
| A61K 35/747 | (2015.01) |
| C12R 1/25 | (2006.01) |
| A23L 33/135 | (2016.01) |
| A23L 33/00 | (2016.01) |
| A61P 1/14 | (2006.01) |
| C12N 1/20 | (2006.01) |
| A23C 9/123 | (2006.01) |
| A61K 9/00 | (2006.01) |
| A23L 11/50 | (2021.01) |
| A23L 11/65 | (2021.01) |

(52) U.S. Cl.
CPC .......... *A61K 35/747* (2013.01); *A23C 9/1234* (2013.01); *A23L 11/50* (2021.01); *A23L 11/65* (2021.01); *A23L 33/135* (2016.08); *A23L 33/40* (2016.08); *A61K 9/0056* (2013.01); *A61P 1/14* (2018.01); *C12N 1/205* (2021.05); *A23V 2002/00* (2013.01); *A23Y 2220/67* (2013.01); *C12R 2001/25* (2021.05)

(58) Field of Classification Search
None
See application file for complete search history.

(56) References Cited

U.S. PATENT DOCUMENTS 9,763,988 B2 * 9/2017 Kim ...................... A23L 33/135

* cited by examiner

*Primary Examiner* — Vera Afremova
(74) *Attorney, Agent, or Firm* — Idea Intellectual Limited; Margaret A. Burke; Sam T. Yip

(57) ABSTRACT

The present invention relates to the technical field of microbes, in particular to a *Lactobacillus plantarum* which can significantly inhibit the occurrence of colorectal cancer, and its use thereof. The *Lactobacillus plantarum* strain CCFM164 has a deposit number CGMCC No. 14520, which has a good tolerance to gastric acid and bile salts, significantly alleviate the level of colorectal inflammation in colorectal cancer model mice, and can reduce the number of tumors in the colon and rectum of the model mice by regulating the Notch1, Notch2 signaling pathway and the expression of VEGFR2 molecule in colorectal tissue. In addition, the *Lactobacillus plantarum* CCFM164 can also improve the intestinal flora population and short-chain fatty acid levels in the intestine. The *Lactobacillus plantarum* CCFM164 is used to prepare a fermented food for the inhibition of the occurrence of colorectal cancer with wild applications.

2 Claims, 8 Drawing Sheets
Specification includes a Sequence Listing.

A: Blank group
B: Model group
C: CCFM164 group
D: LP60 group
E: E.coli group

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 1
attgccgaca ggatgcagaa                                           20

<210> SEQ ID NO 2
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 2
gctgatccac atctgctgga                                           20

<210> SEQ ID NO 3
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 3
gctgatggcc ctaaacagat g                                         21

<210> SEQ ID NO 4
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 4
tggtggtcgg agattcgtag                                           20
```

<210> SEQ ID NO 5
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 5
tccagcctca ccactcacaa g                                          21

<210> SEQ ID NO 6
<211> LENGTH: 25
<212> TYPE: DNA
<213> ORGANISM: Artificial Sequence
<220> FEATURE:
<223> OTHER INFORMATION: Synthesized in the lab

<400> SEQUENCE: 6
ttcatttcat cttcaccaca actcc                                      25

<210> SEQ ID NO 7
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 7
aaaaatgggg ccaaccgaga c                                          21

<210> SEQ ID NO 8
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 8
ttcatccaga aggcgcacaa                                            20

<210> SEQ ID NO 9
<211> LENGTH: 22
<212> TYPE: DNA
<213> ORGANISM: Artificial Sequence
<220> FEATURE:
<223> OTHER INFORMATION: Synthesized in the lab

<400> SEQUENCE: 9
actgtcatcc ttaccaatcc ca                                         22

<210> SEQ ID NO 10
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 10
atctggggtg ggacatacac                                            20

<210> SEQ ID NO 11
<211> LENGTH: 20
<212> TYPE: DNA
<213> ORGANISM: Artificial Sequence
<220> FEATURE:

<223> OTHER INFORMATION: Synthesized in the lab

<400> SEQUENCE: 11
acagccactc acctcttcag                                           20

<210> SEQ ID NO 12
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 12
gcctctttgc tgctttcaca                                           20

<210> SEQ ID NO 13
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 13
tacagccacc atgagaagga c                                         21

<210> SEQ ID NO 14
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 14
tgatcgtctt tagcctttcc a                                         21

<210> SEQ ID NO 15
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 15
gctgcgaagt ggaaaccatc                                           20

<210> SEQ ID NO 16
<211> LENGTH: 22
<212> TYPE: DNA
<213> ORGANISM: Artificial Sequence
<220> FEATURE:
<223> OTHER INFORMATION: Synthesized in the lab

<400> SEQUENCE: 16
cctccttctg cacacatttg aa                                        22

<210> SEQ ID NO 17
<211> LENGTH: 23
<212> TYPE: DNA
<213> ORGANISM: Artificial Sequence
<220> FEATURE:
<223> OTHER INFORMATION: Synthesized in the lab

<400> SEQUENCE: 17
catctacaca gtttgatgct gct                                       23

```
<210> SEQ ID NO 18
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 18
gcagttttgt cagttcaggg a                                              21

<210> SEQ ID NO 19
<211> LENGTH: 22
<212> TYPE: DNA
<213> ORGANISM: Artificial Sequence
<220> FEATURE:
<223> OTHER INFORMATION: Synthesized in the lab

<400> SEQUENCE: 19
atcttcttgt ccggctgtta ca                                             22

<210> SEQ ID NO 20
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 20
gtcctcggcg aacttgtcat t                                              21

<210> SEQ ID NO 21
<211> LENGTH: 19
<212> TYPE: DNA
<213> ORGANISM: Artificial Sequence
<220> FEATURE:
<223> OTHER INFORMATION: Synthesized in the lab

<400> SEQUENCE: 21
cggacatcaa cgacgtgag                                                 19

<210> SEQ ID NO 22
<211> LENGTH: 19
<212> TYPE: DNA
<213> ORGANISM: Artificial Sequence
<220> FEATURE:
<223> OTHER INFORMATION: Synthesized in the lab

<400> SEQUENCE: 22
gacgccttca gcacgaact                                                 19

<210> SEQ ID NO 23
<211> LENGTH: 19
<212> TYPE: DNA
<213> ORGANISM: Artificial Sequence
<220> FEATURE:
<223> OTHER INFORMATION: Synthesized in the lab

<400> SEQUENCE: 23
tggccttccg tgttcctac                                                 19

<210> SEQ ID NO 24
<211> LENGTH: 20
<212> TYPE: DNA
<213> ORGANISM: Artificial Sequence
<220> FEATURE:
<223> OTHER INFORMATION: Synthesized in the lab
```

```
<400> SEQUENCE: 24
gagttgctgt tgaagtcgca                                              20

<210> SEQ ID NO 25
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 25
tcaacacgac accggacaaa                                              20

<210> SEQ ID NO 26
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 26
atgccgggag ctatctttct t                                            21

<210> SEQ ID NO 27
<211> LENGTH: 19
<212> TYPE: DNA
<213> ORGANISM: Artificial Sequence
<220> FEATURE:
<223> OTHER INFORMATION: Synthesized in the lab

<400> SEQUENCE: 27
cccttgctct gcctaacgc                                               19

<210> SEQ ID NO 28
<211> LENGTH: 19
<212> TYPE: DNA
<213> ORGANISM: Artificial Sequence
<220> FEATURE:
<223> OTHER INFORMATION: Synthesized in the lab

<400> SEQUENCE: 28
ggagtcctgg catcgttgg                                               19

<210> SEQ ID NO 29
<211> LENGTH: 22
<212> TYPE: DNA
<213> ORGANISM: Artificial Sequence
<220> FEATURE:
<223> OTHER INFORMATION: Synthesized in the lab

<400> SEQUENCE: 29
aacattgggt tgatgatgaa gg                                           22

<210> SEQ ID NO 30
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 30
gaggagtgag tgccagggat                                              20

<210> SEQ ID NO 31
<211> LENGTH: 21
```

```
<212> TYPE: DNA
<213> ORGANISM: Artificial Sequence
<220> FEATURE:
<223> OTHER INFORMATION: Synthesized in the lab

<400> SEQUENCE: 31
gcagaagcag cacgaagtgt t                                      21

<210> SEQ ID NO 32
<211> LENGTH: 20
<212> TYPE: DNA
<213> ORGANISM: Artificial Sequence
<220> FEATURE:
<223> OTHER INFORMATION: Synthesized in the lab

<400> SEQUENCE: 32
ggaagatgta ctcgatctca                                        20
```

LACTOBACILLUS PLANTARUM WITH COLORECTAL CANCER INHIBITION FUNCTION AND USE THEREOF

CROSS-REFERENCES TO RELATED APPLICATIONS

This application is a 371 application of the International Patent Application No. PCT/CN2018/092671 filed on Jul. 19, 2018, which claims priority from the Chinese patent application No. 201711068300.3 filed on Nov. 3, 2017, and the disclosures of which are incorporated herein by reference in their entirety.

FIELD OF THE INVENTION

The invention relates to the technical field of microbes, in particular to a kind of *Lactobacillus plantarum* which can significantly inhibit the occurrence of colorectal cancer by regulating Notch1, Notch2, and VEGFR2 signaling pathways and uses thereof.

BACKGROUND OF THE INVENTION

Colorectal cancer is a malignant gastrointestinal tumor. With the continuous rise of incidence rate and mortality rate of colorectal cancer in China, the threat to the health of nationals is gradually increasing. At present, the main treatment methods for colorectal cancer in clinical practice have serious side effects, which greatly affects the quality of life of patients. As a safe and edible food, probiotics have been gradually proved to be effective in relieving and treating various disease, such as promoting digestion and absorption, enhancing immunity, preventing infections in reproductive system, relieving allergic reactions, preventing and inhibiting tumors, cardiovascular and cerebrovascular diseases, neurological diseases, etc.

The intestine is not only the direct disease area of colorectal cancer, but also the main place where probiotics exert their probiotic effects. The research on the effects of probiotics for colorectal cancer is gradually increasing. Some studies have shown that probiotics, especially lactic acid bacteria, have the effect of antagonizing colon cancer cells or inhibiting colon cancer. They can inhibit the proliferation of colon cancer cells or induce the apoptosis of colon cancer cells at different levels. In addition, the antagonistic effect of probiotics on colorectal cancer is shown in the following aspects: combining or metabolizing carcinogens, inducing apoptosis of cancer cells, improving immunity, inhibiting the differentiation and proliferation of cancer cells, protecting the intestine, and maintaining intestinal flora balance, etc., while the regulation of probiotics on the intestinal flora will eventually affect the concentration of short-chain fatty acids in the intestine, further affecting the occurrence of tumors.

Some studies have shown that despite the higher concentration of butyrate in the colon, colon cancer can still develop and grow, and the butyrate-rich microenvironment can select the tumor cells which can metabolize butyrate. Probiotics may also inhibit tumorigenesis by regulating tumor-related signaling pathways. There are many signaling pathways involved in colorectal cancer, including AKT signaling pathway, GPCR signaling pathway, MAPK signaling pathway, NF-κB signaling pathway, JAK signaling pathway, Wnt signaling pathway, TGF-β signaling pathway, ESC signaling pathway, apoptosis signaling pathway, CCC signaling pathway and angiogenesis signaling pathway, etc.

At present, many studies focused on the relationship between Wnt and NF-κB signaling pathways and colorectal cancer. However, Notch signaling pathway, as a signaling pathway related to epithelial cell differentiation, is also closely related to the colorectal cancer. For the colorectal cancer, the Notch signaling pathway plays a role in inducing and promoting tumors to increase drug resistance. Many clinical studies have also shown that the Notch signaling pathway in colon tumor tissue is over activated compared with that in adjacent or normal tissues.

In addition to the Notch signaling pathway, numerous studies have also shown that vascular endothelial growth factor receptor (VEGFR) is highly expressed in most tumors. Most of the main physiological functions of VEGF on endothelial cells are achieved by activating VEGFR2, including stimulating endothelial cell proliferation, increasing vascular permeability, and inducing the chemotaxis of endothelial cells. Researchers have observed that in a variety of endothelial cells, the combination of VEGF and VEGFR2 activates the MAPK signal transduction pathway. VEGFR2 not only promotes the division and proliferation of vascular endothelial cells, but also induces tumor angiogenesis and promotes the growth and metastasis of tumor cells. A large number of reports also show that VEGFR2 is also highly expressed in colorectal cancer tissues. Therefore, VEGFR2 can be used as a target for the treatment and diagnosis of tumorigenesis.

Probiotics may also regulate the Notch signaling pathway and the levels of VEGFR2, so as to alleviate the occurrence of colorectal cancer or inhibit the growth of colon cancer cells. *Lactobacillus plantarum* is a kind of lactic acid bacteria, which is widely present on the surface of fruits and vegetables, as well as in pickles and other traditional fermented foods. There are lots of research reports regarding the physiological functions of *Lactobacillus plantarum*, but there are still few functional studies and patents for the inhibition of colorectal cancer by *Lactobacillus plantarum*. The research on the inhibition of colorectal cancer by *Lactobacillus plantarum* is of great value to the fields such as food science, preventive medicine and microbiology. Screening an excellent *Lactobacillus plantarum* with the safety and the function for inhibition of the colorectal cancer is of great significance for the development of functional foods and drugs.

In the published literatures and patents or patent applications, there are a few number of patents regarding probiotics, probiotic composition and fermentation products to suppress tumors, but there is no clear probiotic strain with the function of colon cancer inhibition. For example, CN105535650A discloses a probiotic composition with anti-tumor (subcutaneous transplantation of liver cancer cell line) function. The composition relates to a variety of probiotics and traditional Chinese medicine ingredients, but the tumor inhibition function of each ingredient is not clear, and all probiotics strains have not been identified. Since there are significant functional differences between different strains of the same probiotics, therefore the composition do not have general and universal effect; Meanwhile, the strains of probiotics in CN104686657A and CN101711775A have not been identified, and the function of the ingredients in the fermentation products is not clear.

CN104523761A disclosed a genetically engineered *Lactococcus lactis* that can induce the expression of Interleukin-12 to inhibit the growth of intestinal tumors. However such bacteria are not obtained from nature and can only be applied to medicines but not for food. CN105441357A discloses a strain SKT109 of *Lactobacillus plantarum*, which can produce extracellular polysaccharides to inhibit the growth of human colon cancer cells HT-29 in vitro and inhibit the growth of tumors in tumor-bearing nude mice (colon cancer cells inoculated under the arm); CN103445068A and CN103468600A disclosed a strain DY-1 of *Lactobacillus plantarum*, which can inhibit the in vitro growth of human colon cancer cells HT-29, gastric cancer cells SGC-7901 and growth of tumor in tumor-bearing nude mice (subcutaneously inoculation of colon cancer cells in abdomen). The above three patented strains are definite and have clear functions, but the concerned animal models with subcutaneous colon cancer cell lines is quite different from the tumor environment in the intestine, and it has no clear role in the regulation of tumor-related signaling pathways. Therefore, there is a need to screen edible probiotics with clear inhibition mechanism from nature to inhibit the growth of colorectal tumors.

SUMMARY OF THE INVENTION

In view of the above problems in the prior art, the present application provides a *Lactobacillus plantarum* and its use thereof. This strain has a strong ability to regulate the Notch1, Notch2 signaling pathway and the expression of the VEGFR2 molecule, which can significantly inhibit the occurrence of colorectal cancer, and can also alleviate colorectal inflammation, improve the populations of intestinal flora and the levels of the short chain fatty acids.

The technical solution of the present invention is as follows:

A *Lactobacillus plantarum* CCFM164 (*Lactobacillus plantarum*) was deposited in the China General Microbiological Culture Collection Center CGMCC on Aug. 11, 2017. The deposit address is Institute of Microbiology, Chinese Academy of Sciences, No. 3, No. 1 Institute, Beichen West Road, Chaoyang District, Beijing. The deposit number is CGMCC No. 14520.

A fermented food is fermented by *Lactobacillus plantarum* CCFM164, wherein the fermented food is a fermented dairy product, a fermented soy product, and a fermented fruit and vegetable product.

The dairy product includes milk, sour milk oil or cheese; the soy product includes soy milk, tempeh or soy sauce, and the fruit and vegetable product includes cucumber, carrot, beet, celery or cabbage.

An application of *Lactobacillus plantarum* CCFM164 or fermented food is used to improve the intestinal flora, reduce the abnormally high levels of short chain fatty acids in the intestine, alleviate colorectal inflammation and inhibit the occurrence of colorectal cancer.

The *Lactobacillus plantarum* CCFM164 has the following biological characteristics:

(1) Bacterial characteristics: it is gram-positive bacteria and acid resistant. It grows well in the environment with pH from 3.0 to 7.2 and does not form spores. The cell is about (0.9 to 1.2)μm×(3.0 to 8.0)μm, bacilli shaped bacterium, single, paired or short chain, usually lacking flagella but able to move.

(2) Colony characteristics: the obvious colonies are formed on the MRS medium with diameter between 0.3 to 3.0 mm, round, convex or lens-shaped, fine and white, with a smooth to mucus-like soft surface, and no mycelium is formed.

(3) Growth characteristics: the bacteria are facultative anaerobic bacteria with the optimal growth temperature of 36 to 38° C., and the bacteria can grow well at 32 to 38° C., and can also grow at 15° C. The optimal initial pH is 6-7. It grows well in the glucose-containing culture medium;

(4) Good tolerance to artificial gastrointestinal fluid;

(5) It can regulate the Notch1 and Notch2 signaling pathway and the expression level of VEGFR2 in HT-29 cells;

(6) It can significantly reduce the number of tumors in colorectal cancer tissue of colon cancer model mice and improve the integrity of intestinal tissues of the model mice;

(7) It can significantly alleviate the level of colorectal inflammation in colon cancer model mice;

(8) It can regulate the Notch1 and Notch2 signaling pathway and the expression level of VEGFR2 in colon tissue of colon cancer model mice;

(9) It can improve the intestinal microecology and short chain fatty acids in colon cancer model mice.

The extraction method of this strain is as follows:

(A) Isolation and screening of lactic acid bacteria (1) Collect several feces of healthy people and pickles, and enrich the samples in sorbitol-containing MRS medium for 12 h;

(2) Dilute the enriched samples gradiently and apply them to the MRS solid plate supplemented with 0.02% bromocresol purple, and incubate the plate for 24-48 h;

(3) Select single colony with obvious color circle, and the single colony with the baic morphology of lactic acid bacteria was purified by plate scribing, and then select and isolate the lactic acid bacteria;

(4) The above single colony was cultured in the liquid MRS culture medium for 24 h and performed Gram staining, and then the Gram-positive bacteria were selected for subsequent experiments.

(B) Preliminary identification of *Lactobacillus plantarum*: calcium dissolving circle assay (1) Culture the lactic acid bacteria that was selected in step (1) in the liquid sorbitol MRS culture medium for 24 h, and then take 1 mL of the culture and centrifuge at a speed of 8000 rpm for 2 minutes;

(2) Wash twice with 0.05M $KH_2PO_4$ solution;

(3) Resuspend the obtained bacteria slurry, and streak on the solid culture plate with sorbitol MRS-0.75% $CaCO_3$, and culture for 24 hours;

(4) Select the colonies with obvious calcium dissolving circles, round convex surface, fine and white, and no mycelium is formed. After completion of Gram staining, the bacteria with rod-shaped under the microscope was initially determined as a *Lactobacillus*.

(C) Molecular biological identification of *Lactobacillus plantarum*

(1) Extraction of single bacterial genome a. Incubate the lactic acid bacteria in step (B) overnight, and transfer 1 mL of the overnight cultured bacterial suspension into a 1.5 mL centrifuge tube, then centrifuge at a speed of 10,000 rpm for 2 minutes, after that discard the supernatant to obtain bacteria;

b. After washing the bacteria with 1 mL of sterile water, centrifuge at a speed of 10,000 rpm for 2 minutes, and discard the supernatant to obtain the bacteria; c. Add 200 μL of SDS lysis buffer, and put it in a 80° C. water bath for 30 minutes;

d. Add 200 μL of phenol-chloroform solution into the bacterial lysis buffer, where the components and the volume ratio of the phenol-chloroform solution are as Tris-saturated phenol:chloroform:isoamyl alcohol=25:

24:1. After upside down mixing, centrifuge the solution at a speed of 12,000 rpm for 5 to 10 minutes, and obtain 200 μL of supernatant;

e. Add 400 μL of ice-cold ethanol or ice-cold isopropanol into the 200 μL supernatant and keep at −20° C. for 1 hour, followed by centrifuging the supernatant at a speed of 12,000 rpm for 5 to 10 minutes, and discard the supernatant;

f. Add 500 μL of ice-cold 70% ethanol (volume percentage) for resuspension and precipitation of the supernatant at a speed of 12,000 rpm for 1 to 3 minutes, and discard the supernatant;

g. Dry the pellets in an oven at a temperature of 60° C., or dry the pellets naturally;

h. Re-dissolve the pellets in 50 μL of ddH$_2$O for the subsequent PCR reaction; (2) 16S rDNA PCR a. 50 μL PCR reaction solution of 16 S rDNA of bacteria: 10×Taq buffer, 5 μL; dNTP, 5 μL; 27 F, 0.5 μL; 1492R, 0.5 μL; Taq polymerase, 0.5 μL; template, 0.5 μL; ddH$_2$O, 38 μL.

b. PCR conditions:

95° C. 5 minutes; 95° C. 10 seconds; 55° C. 30 seconds; 72° C. 30 seconds; step 2 to 4 30×; 72° C. 5 minutes; 12° C. 2 minutes;

(3) Prepare 1% of agarose gel, then mix the PCR products with 10000×loading buffer, and then load 5 μL of the sample mixture onto the agarose gel and run at 120V for 30 minutes, followed by performing gel imaging;

(4) Sequence and analyze the 16S rDNA PCR products, and the sequencing results were subjected to similarity comparison by BLAST software among GeneBank database, then the selected lactic acid bacteria was identified as *Lactobacillus plantarum* by the sequencing results, and store it at −80° C.;

The present invention has the following advantages: The *Lactobacillus plantarum* CCFM164 of the present invention has a good tolerance to gastric acid and bile salts, and can regulate Notch1, Notch2 signaling pathway and the expression levels of the VEGFR2 molecule in colorectal tissue so as to achieve the inhibition on colorectal cancer, significantly alleviates the level of colorectal inflammation in colorectal cancer model mice, and reduce the number of tumors in the colon and rectum of the mice. In addition, the *Lactobacillus plantarum* CCFM164 of the present invention can also improve the intestinal flora and the levels of short-chain fatty acid in the intestine.

The present strain is superior to the commercial strain-*Lactobacillus rhamnosus* GG (LGG) in inhibiting the occurrence of colorectal cancer. Further, the mechanism of inhibiting the occurrence of colorectal cancer is different from LGG strain. Therefore, the *Lactobacillus plantarum* CCFM164 of the present invention can be applied as an auxiliary manner for clinical treatment of colorectal cancer without any toxic and side effects. The *Lactobacillus plantarum* CCFM164 can be used to prepare pharmaceutical compositions and fermented foods, which can relieve and prevent the occurrence of colorectal cancer with wilde applications.

DETAILED DESCRIPTION

Figure 1:
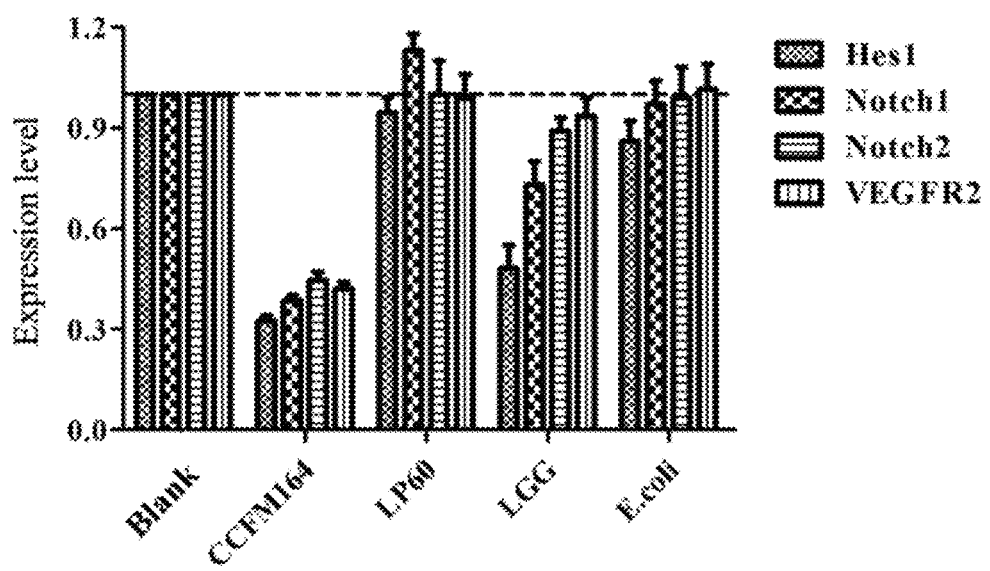
FIG. 1 depicts the effect of the claimed strain on the Notch1, Notch2 signaling pathway and the expression of the VEGFR2 in HT-29 cell lines.

Detailed description to the present invention is provided with drawings, embodiments and examples as follows.

Example 1: *Lactobacillus plantarum* CCFM164 has Good Tolerance to the Simulated Gastrointestinal Fluid The frozen *Lactobacillus plantarum* CCFM164 was streaked and inoculated on a MRS solid plate, and the plate was incubated at 37° C. for 24 hours under aerobic cultivation, followed by 2 to 3 times subculture in the MRS culture medium. The culture medium with *Lactobacillus plantarum* CCFM164 was collected and centrifuged at a speed of 8000×g for 5 minutes to obtain bacteria, and then resuspended and mixed (1:1) in pH 2.5 of artificial simulated gastric juice (MRS medium containing 1% pepsin, pH 2.5), followed by anaerobic cultivation at 37° C. The samples were collected at the beginning (0 h), 1 h, 2 h, and 3 h, respectively, and the sample were cultured on MRS medium agar plate for colony counting. The viability numbers can be counted and the survival rates can be calculated accordingly. The survival rate is the rate of the viable count at the desired time point to the viable count at the 0 hour, which is expressed in %.

The medium cultured with the strain of *Lactobacillus plantarum* CCFM164 was taken and centrifuged at a speed of 8000×g for 5 minutes. The bacteria were collected and resuspended (1:1) in artificial simulated intestinal fluid (MRS medium containing 0.3% bile salts from ox, 1% trypsin, pH 8.0), followed by aerobic cultivation at 37° C. The samples were collected at the 0 h, 1 h, 2 h, 3 h, and 4 h, respectively, and the samples were cultured on MRS medium agar plate for colony counting. The viability numbers can be counted and the survival rates can be calculated accordingly. The survival rate is the rate of the viable count at the desired time point to the viable count at the 0 hour, which was expressed in %. The experiment results were shown in Table 1 and Table 2. The results showed that *Lactobacillus plantarum* CCFM164 has a good tolerance to artificial simulated gastrointestinal fluid and intestinal fluid.

TABLE 1

Tolerance of *Lactobacillus plantarum* CCFM164
to simulated gastrointestinal fluid

| Treatment Time (h) | Artificial simulated gastrointestinal fluid | | |
|---|---|---|---|
| | 1 | 2 | 3 |
| Survival Rate (%) | 95.81 ± 2.11 | 92.78 ± 3.19 | 90.66 ± 5.15 |

TABLE 2

Tolerance of *Lactobacillus plantarum* CCFM164
to simulated intestinal fluid

| Treatment | Artificial simulated intestinal fluid | | | |
|---|---|---|---|---|
| Time (h) | 1 | 2 | 3 | 4 |
| Survival Rate (%) | 92.21 ± 4.31 | 82.22 ± 5.28 | 75.82 ± 3.41 | 66.34 ± 6.55 |

Example 2: Regulation of *Lactobacillus plantarum* CCFM164 on Notch1, Notch2, VEGFR2 and Colon Cancer-Related Signaling Pathways in HT-29 Cells The sludges of *Lactobacillus plantarum* CCFM164 (or control group of *Lactobacillus plantarum* LP60, LGG, *E. coli*) were washed twice with PBS and resuspended in RPMI1640 cell culture medium without antibiotics to make the cell density to about $2 \times 10^8$ CFU/mL; 2 mL of the CCFM164 (or LP60, LGG, *E. coli*) suspension was added to a 6 well plate in which HT-29 cells had been cultured in advance (with 95% confluence), and the blank group was added with 2 mL of cell culture medium without antibiotics and placed in a cell incubator containing 5% of $CO_2$ at 37° C. for 2 hours; after the cells were washed 3 times with PBS, 1 mL of TRIzol was added to each well (6 well plate). After being standed at room temperature for 5 minutes, the cells were repeatedly pipetted by an enzyme-free pipetman, then transferred to a 1.5 mL enzyme-free eppendorf, and the total RNAs of the cells were extracted according to the TRIzol instruction manual; a process of reverse transcription was performed in accordance with the Takara RR047A instruction manual; fluorescence-based quantitative PCR was conducted in accordance with the Bio-Rad iTaq Universal SYBR Green Supermix instruction manual, and the primers used herewith were shown in Table 3.

TABLE 3 qPCR primer sequence

| Primer name | Primer sequence (5'-3') |
|---|---|
| GAPDH (H) | F: ATTGCCGACAGGATGCAGAA |
| | R: GCTGATCCACATCTGCTGGA |
| Hes1 (H) | F: GCTGATGGCCCTAAACAGATG |
| | R: TGGTGGTCGGAGATTCGTAG |
| Notch1 (H) | F: TCCAGCCTCACCACTCACAAG |
| | R: TTCATTTCATCTTCACCACAACTCC |
| Notch2 (H) | F: AAAAATGGGGCCAACCGAGAC |
| | R: TTCATCCAGAAGGCGCACAA |
| VEGFR2 (H) | F: ACTGTCATCCTTACCAATCCCA |
| | R: ATCTGGGGTGGGACATACAC |

TABLE 3-continued qPCR primer sequence

| Primer name | Primer sequence (5'-3') |
|---|---|
| p21 (H) | F: ACAGCCACTCACCTCTTCAG |
| | R: GCCTCTTTGCTGCTTTCACA |
| MYC (H) | F: TACAGCCACCATGAGAAGGAC |
| | R: TGATCGTCTTTAGCCTTTCCA |
| CyclinD1 (H) | F: GCTGCGAAGTGGAAACCATC |
| | R: CCTCCTTCTGCACACATTTGAA |
| β-catenin (H) | F: CATCTACACAGTTTGATGCTGCT |
| | R: GCAGTTTTGTCAGTTCAGGGA |
| FZD1 (H) | F: ATCTTCTTGTCCGGCTGTTACA |
| | R: GTCCTCGGCGAACTTGTCATT |
| KLF4 (H) | F: CGGACATCAACGACGTGAG |
| | R: GACGCCTTCAGCACGAACT |

Figure 2:
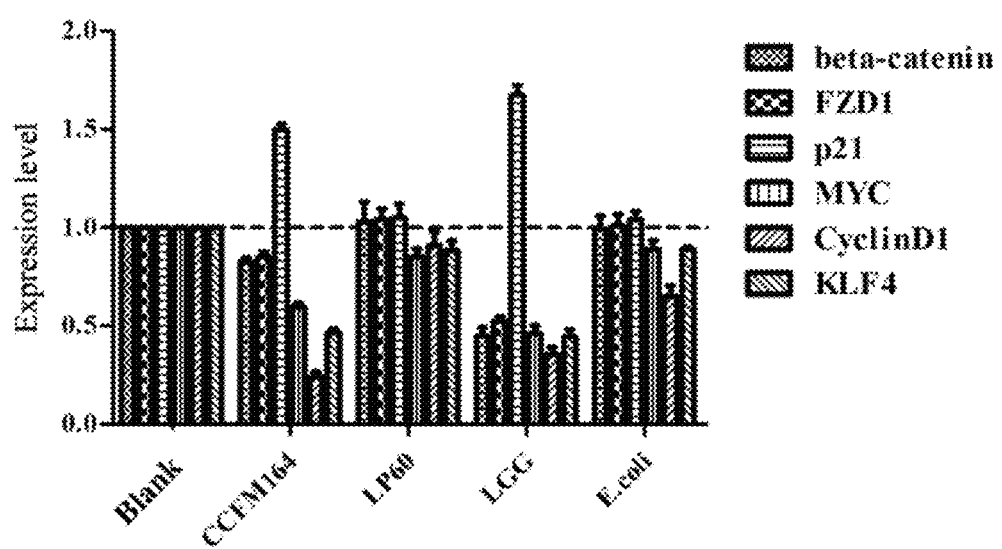
FIG. 2 depicts the effect of the claimed strain on the expression level of other cancer-related signaling pathways in HT-29 cell lines.

The results were shown in FIG. 1 and FIG. 2. The *Lactobacillus plantarum* CCFM164 showed a downregulation at the transcription levels of Notch1, Notch2, Hes1, and VEGFR2 genes in HT-29 cells, while LGG only showed a certain downregulation at the transcription levels of Notch1 and Hes1 genes, but LGG did not show a significant downregulation of Notch2 and VEGFR2; the *Lactobacillus plantarum* CCFM164 also significantly inhibited the transcription of Notch1 and Hes1 in comparison with LGG; the *Lactobacillus plantarum* LP60 and *E. coli* did not significantly downregulate the transcription levels of Notch1, Notch2, Hes1 and VEGFR2, and LP60 upregulated the expression level of Notch1 instead. Test results for other tumor-related signaling molecules indicated that the transcriptional regulation of LGG on tumor-related signaling molecules, except for Notch1/2, VEGFR2, CyclinD1, and KLF4, was stronger than the *Lactobacillus plantarum* CCFM164. It means that not all strains of *Lactobacillus plantarum* can inhibit the occurrence of colorectal cancer, and the inhibition mechanism of *Lactobacillus plantarum* CCFM164 to the occurrence of colorectal cancer is also different from LGG. The *Lactobacillus plantarum* CCFM164 mainly achieves the occurrence of colorectal tumors by regulating the levels of Notch signaling pathway and the level of VEGFR2. For example, *E. coli* in the control group only showed a certain downregulation at the transcription level of CyclinD1 but did not affect other molecules, and the *Lactobacillus plantarum* LP60 did not significantly affect the transcription levels of other molecules.

Example 3: *Lactobacillus plantarum* CCFM164 has No Toxic and Side Effects on Mice The *Lactobacillus plantarum* CCFM164 were resuspended in 2% (w/v) of sucrose solution to give a bacterial suspension with a concentration of $4.0 \times 10^9$ CFU/mL. 10 healthy male BALB/c mice with a weight about 25 g were chosen and administered with above bacteria suspension by intragastric gavage once daily. The death and weight of the mice were observed and recorded for one week.

The results were shown in Table 4, which showed that administration of the *Lactobacillus plantarum* CCFM164 with a concentration of $4.0 \times 10^9$ CFU/mL did not have significant influences on mice. There was no significant change in body weight and death of mice, and there was no obvious pathological symptom in the appearance of the mice.

TABLE 4

| | Changes in body weight and death of mice | | | | | | |
|---|---|---|---|---|---|---|---|
| Time (day) | 1 | 2 | 3 | 4 | 5 | 6 | 7 |
| Weight (g) | 25.5 ± 1.6 | 25.5 ± 1.7 | 25.6 ± 1.5 | 25.6 ± 1.6 | 25.7 ± 1.8 | 25.6 ± 1.9 | 25.7 ± 1.9 |
| Death | — | — | — | — | — | — | — |

Note:
"—", no death of mice.

Example 4: Alleviating Effect of *Lactobacillus plantarum* CCFM164 on Colorectal Cancer of Mice 48 healthy male BALB/c mice with weight from 20 to 25 g were chosen and divided into 6 groups randomly: blank control group, colorectal cancer model control group, *Lactobacillus plantarum* CCFM164 intervention group, *Lactobacillus plantarum* LP60 control group, LGG control group, *E. coli* control group, and 8 mice per group.

The model control group, *Lactobacillus plantarum* CCFM164 intervention group, *Lactobacillus plantarum* LP60 control group, LGG control group and *E. coli* control group were developed colorectal cancer models by an AOM-DSS method. That is, after initial AOM intraperitoneal injection (7.5 mg/kg), 2% (m/v) DSS was given in the drinking water for 4 days followed by regular drinking water for 7 days; and mice were subjected to a second DSS cycle with 2% (m/v) DSS given in the drinking water for 4 days followed by regular drinking water for 15 days.

During the process of modeling, the mice in the intervention groups were administered with 0.25 mL suspension of *Lactobacillus plantarum* CCFM164 prepared according to Example 3 of the present invention with a concentration of $4.0 \times 10^9$ CFU/mL, while the mice in the LP60 control group were administered with an equal amount of LP60, the mice in LGG control group were administered with an equal amount of LGG, the mice in *E. coli* control group were administered with an equal amount of *E. coli*, and the remaining 2 groups were administered with an equal amount of 2% (w/v) bacteria-free sucrose solution.

After completion of developing the model, the serum, colon and rectum of model mice were taken, where the colon and rectum were cut along the axis for calculation of the number of tumors. Meanwhile, the colon tissues were taken and prepared as paraffin sections, then stained through HE staining.

Figure 3:
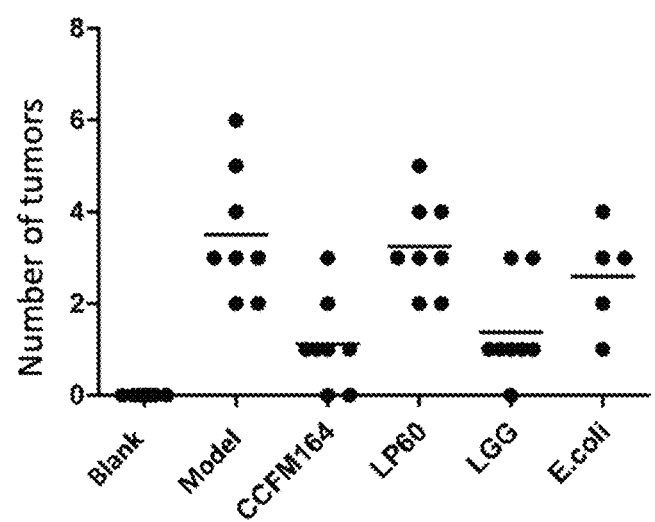
FIG. 3 depicts the effect of the claimed strain on the number of colorectal tumors in colorectal cancer model mice.
Figure 4:
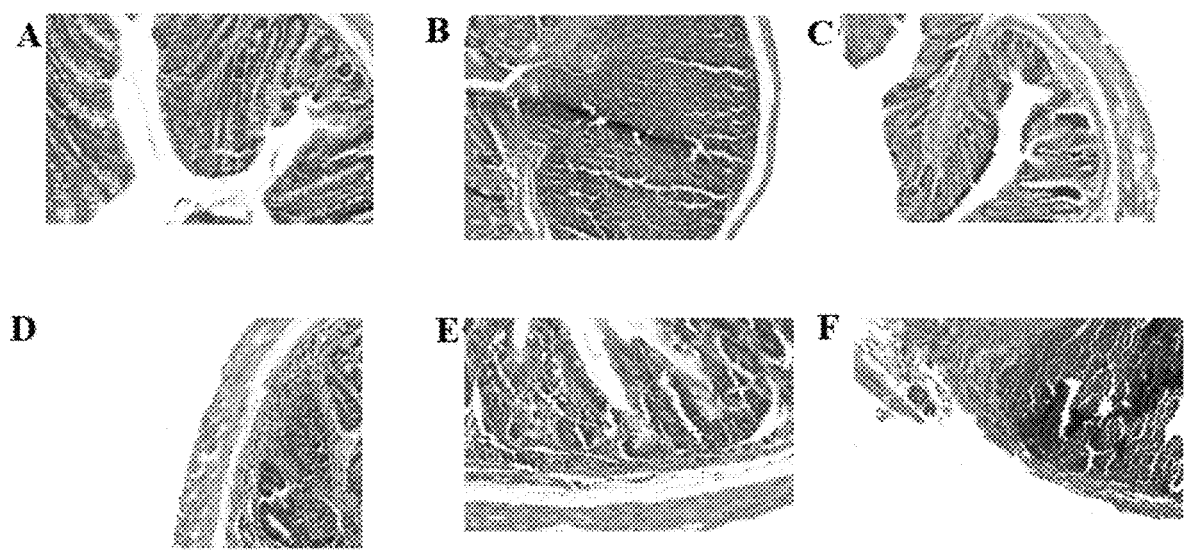
FIG. 4 depicts the recovery of the claimed strain on the damage colorectal tissue of the colorectal cancer model mice.

The results of tumor numbers were shown in FIG. 3. It could be seen by comparing the blank control group and the model control group that the AOM-DSS method could induce mice to develop colorectal cancer. The results showed that the intervention group which was intragastric administrated the *Lactobacillus plantarum* CCFM164 claimed in the present invention could significantly reduce the number of tumors, and the effect of the *Lactobacillus plantarum* CCFM164 was better than LGG. However, the inhibitory effect of LP60 and *E. coli* on tumorigenesis was not obvious, and 3 mice died in the *E. coli* group. H&E staining results were shown in FIG. 4. It could be clearly seen from the slices section that severe lesions had occurred in the model group, LP60 control group and *E. coli* control group. In comparison with the normal mice, malignant proliferating cells had increased significantly, and the tumors had grown inward. The integrity of cell infiltration, tumor or intestinal mucosa after intragastric administration of *Lactobacillus plantarum* CCFM164 has been improved, and the improvement is stronger than the LGG group.

Example 5: Regulation of *Lactobacillus plantarum* CCFM164 on the Colitis-Associated Inflammatory Factors in the Serum of Mice with Colorectal Cancer The serum obtained in Example 4 was taken, and the content of cytokines in the serum was measured by a flow cytometer. The concentrations of the colitis-associated inflammatory factors such as IL-17 and IFN-γ were measured in accordance with the manual of the kit (Milliplex Map kit) and the manual of Luminex.

Figure 5:
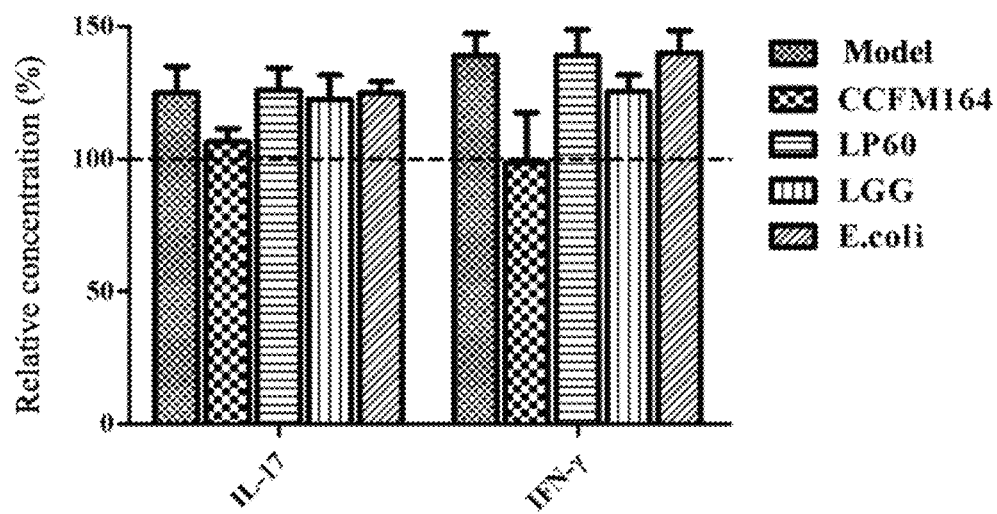
FIG. 5 depicts the improvement of the claimed strain on the levels of IL-17 and IFN-γ in serum of the colorectal cancer model mice.

The results were shown in FIG. 5. In comparison with the blank control group, the levels of IL-17 and IFN-γ in the serum of colorectal cancer model mice were significantly increased (the data corresponding to each column in the figure are the relative concentration of cytokines in the serum compared to the blank control group). The *Lactobacillus plantarum* CCFM164 could significantly reduced the levels of IL-17 and IFN-γ to normal levels, but the LGG, LP60 and *E. coli* had no significant inhibitory effect on the increase of IL-17 and IFN-γ levels.

Example 6: Regulation of *Lactobacillus plantarum* CCFM164 on the Notch 1 and Notch 2 Signaling Pathway and the Expression Level of VEGFR2 in Colon Tissue of the Mice About 1 cm of colon tissue in Example 4 was taken, and 1 mL of TRIzol and 3 steel balls that have been sterilized through dry heat sterilization were added, then a tissue crusher was used to crush the tissue at a frequency of 70 Hz for 30 s as a cycle and repeat 3 times. After that, the solution was transferred to an 1.5 mL RNase-free eppendorf, and the total RNA was extracted, reverse transcribed, and then subjected to qPCR according to the method of Example 2. The primers used herewith are shown in Table 5.

TABLE 5

| qPCR primer sequence | |
|---|---|
| Primer name | Primer sequence (5'-3') |
| GAPDH (M) | F: TGGCCTTCCGTGTTCCTAC |
| | R: GAGTTGCTGTTGAAGTCGCA |
| Hes1 (M) | F: TCAACACGACACCGGACAAA |
| | R: ATGCCGGGAGCTATCTTTCTT |
| Notch1 (M) | F: CCCTTGCTCTGCCTAACGC |
| | R: GGAGTCCTGGCATCGTTGG |
| Notch2 (M) | F: AACATTGGGTTGATGATGAAGG |
| | R: GAGGAGTGAGTGCCAGGGAT |
| VEGFR2 (M) | F: GCAGAAGCAGCACGAAGTGTT |
| | R: GGAAGATGTACTCGATCTCA |

Figure 6:
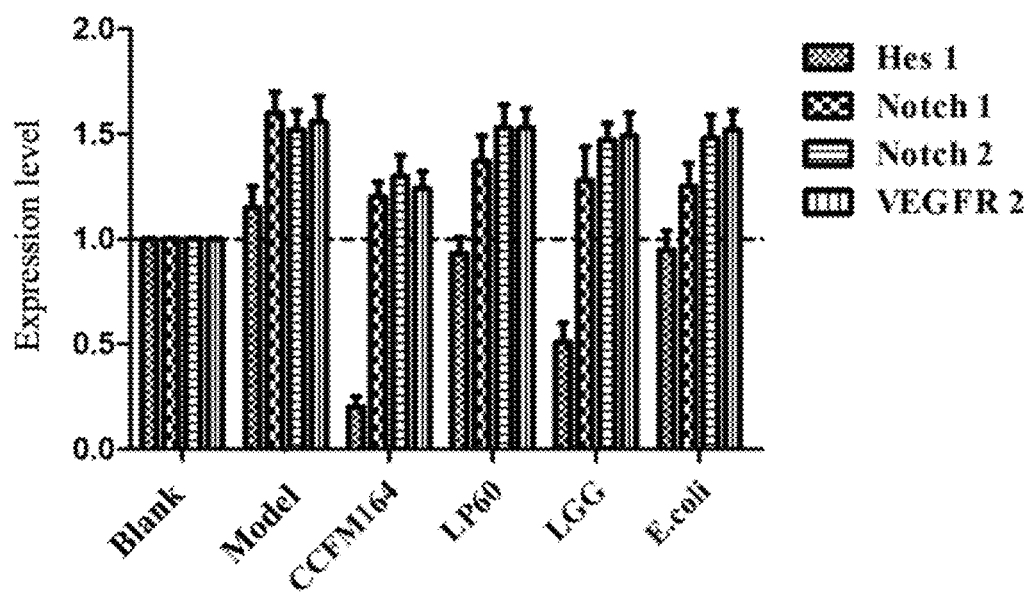
FIG. 6 depicts the effect of the claimed strain on the Notch1 and Notch2 signaling pathway and the expression level of VEGFR2 in intestinal tissue of the colorectal cancer model mice.

The results were shown in FIG. 6. All of LP60, LGG, *E. coli* and *Lactobacillus plantarum* CCFM164 downregulated the transcription levels of the abnormally elevated Notch1 gene in colon tissue of the mice; only the *Lactobacillus plantarum* CCFM164 downregulated the transcription levels of Notch2 gene; only the LGG and *Lactobacillus plantarum* CCFM164 signifigently downregulated the transcription levels of Hest gene in mice, and the effect of the *Lactobacillus plantarum* CCFM164 was better than LGG; only the *Lactobacillus plantarum* CCFM164 signifigently downregulated the transcription levels of VEGFR2.

Example 7: *Lactobacillus plantarum* CCFM164 Downregulated the Expression Level of Butyric Acid in the Intestine of Model Mice 50 mg fecal samples of the mice in Example 4 were taken, and 5004, of saturated NaCl solution was added and adequately shaken with the samples, then 20 μL of 10% sulfuric acid solution was added and adequately shaken again, then 8004, of ether was added and adequately shaken once again; After being centrifuged at a speed of 18000×g, 4° C. for 15 minutes, the supernatant was taken and adequately shaken with 0.25 g of sodium sulfate anhydrous, and the mixture was centrifuged again at a speed of 18000× g, 4° C. for 15 minutes; the supernatant was transferred into a gas bottle for gas analysis.

Figure 7:
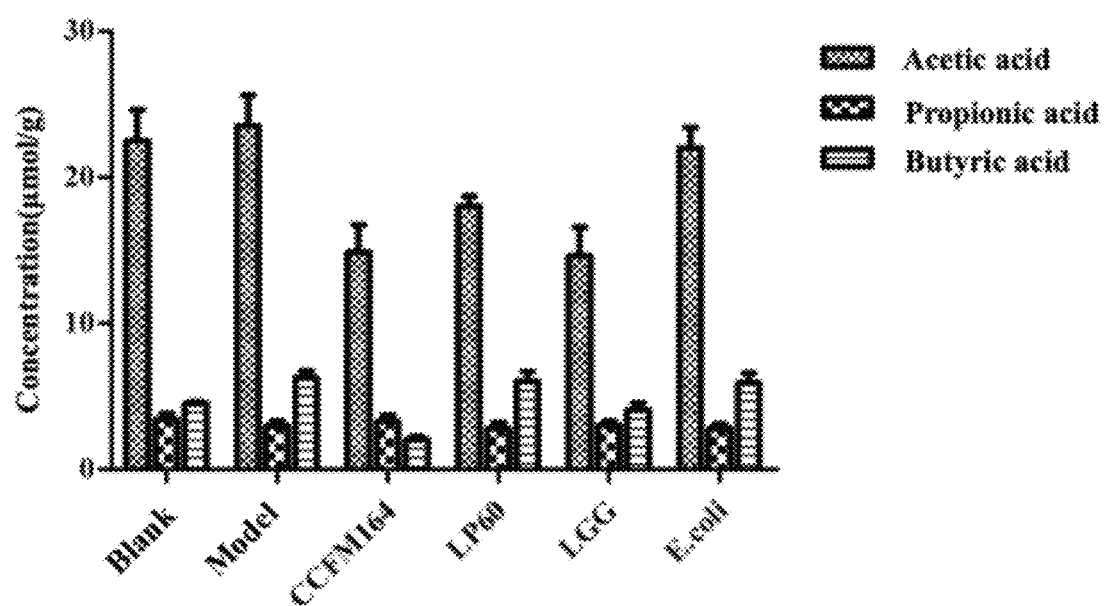
FIG. 7 depicts the effect of the claimed strain on the short chain fatty acids in the intestine of the colorectal cancer model mice.

The results were shown in FIG. 7. There was no significant changes in the content of acetic acid and propionic acid in the intestine of model mice with colon cancer. However, the content of butyric acid increased significantly compared with the blank group. The *Lactobacillus plantarum* CCFM164 and LGG could significantly reduce abnormally elevated levels of butyric acid, and the extent of the *Lactobacillus plantarum* CCFM164 on reducing butyric acid levels was much greater than LGG. The LP60 only had a certain effect on acetic acid, and *E. coli* had no significant effect on the levels of all three acids.

Example 8: Recovery of the *Lactobacillus plantarum* CCFM164 on Dysregulation of Intestinal Flora in Colon Cancer Mouse Model The metagenome of 0.1 g feces of mice in Example 4 were taken and extracted according to the instructions of the kit (FastDNA Spin Kit for Soil) with slight modification, the specific method is shown below. Add about 0.1 g of feces to a Lysing Matrix E tube, and add 978 μL of Sodium Phosphate Buffer and 122 μL of MT Buffer, then stand the tube at room temperature for 30 min; use Fastprep with a speed of 6.0, set the time to 40, and start crushing; centrifuge the mixture at a speed of 14000×g, 4° C. for 10 min and take the supernatant, after that add 250 μL of PPS, mix upside down; centrifuge the mixture at a speed of 14000×g, 4° C. for 10 min and take the supernatant, add 1 mL of Binding Matrix Suspension, mix upside down and take the supernatant, and then add 1 mL of Binding Matrix Suspension. After upside down mixing, leave the mixture at room temperature for 3 minutes, and discard 650 μL of the supernatant. After vortex and resuspension, transfer 650 μL of the suspension to a SPIN Fitter, centrifuge at 14000×g, 4° C. for 2 min, then discard the liquid in the tube and repeat above steps; add 500 μL of SEWS-M (add 100 mL of absolute ethanol before use it and vortex and mix thoroughly), then centrifuge at 14000× g, 4° C. for 1 min and discard the liquid in the tube, after that centrifuge again under the same conditions; use a new liquid collection tube and let it stand at room temperature for 5 minutes; add 50 μL of DES and place it in a metal bath at 55° C. for 5 minutes; then centrifuge at 14000×g, 4° C. for 1 minute, and the DNA solution can be obtained in the liquid collection tube. The obtained DNA solution was sent to a second-generation sequencer for sequencing and analysis.

Figure 8:
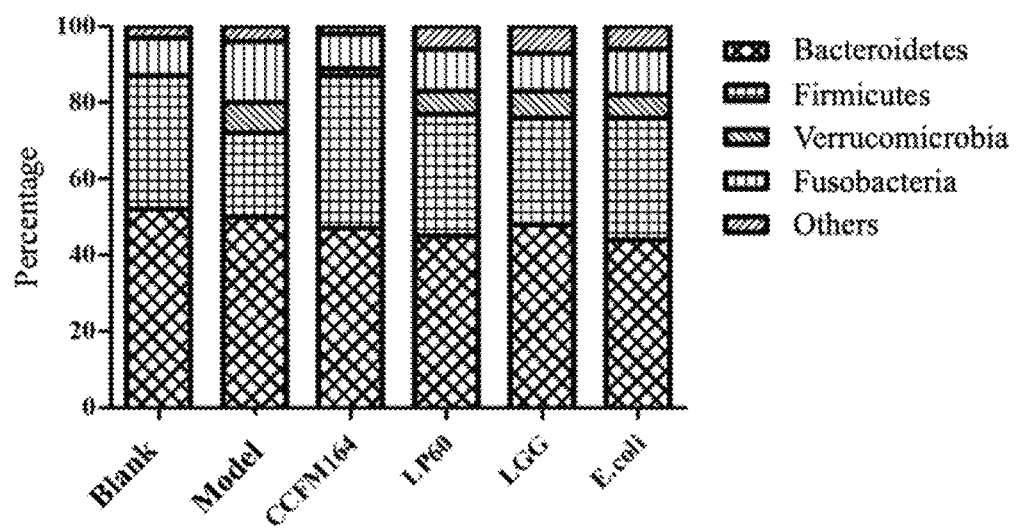
FIG. 8 depicts the improvement of the claimed strain on the population of the intestinal flora of the colorectal cancer model mice.

The results were shown in FIG. 8. The Firmicutes in the intestine of model mice was significantly reduced, while the Verrucomicrobia and Fusobacteria were significantly increased. Ingestion of the *Lactobacillus plantarum* CCFM164 could significantly increase the abundance of Firmicutes in the intestine of model mice and inhibit the abnormally increased Verrucomicrobia and Fusobacteria; LGG could also partially restore the dysfunctional intestinal flora population. However, LGG had no significant inhibitory effect on the abnormally increased Verrucomicrobia, and the abundance of Firmicutes was still low; LP60 or *E. coli* can partially restore the proportion of the Firmicutes, but not other bacteria.

Example 9: Dairy Products Made from *Lactobacillus plantarum* CCFM164 as Claimed in the Present Invention The raw milk (skim milk) was sterilized by heat at 95° C. for 20 min, and cooled to 4° C., and then a *Lactobacillus plantarum* CCFM164 ferment described in the present specification was added to make its concentration reaches $10^6$ CFU/mL or more, and store it under refrigeration at 4° C. Thus, the dairy product containing *Lactobacillus plantarum* CCFM164 as claimed in the present invention was obtained.

Though reference is made to preferred examples for detailed illustration of the present invention and non-limiting thereto, a skilled person in the art should understand that the technical solutions provided by the present invention can be changed or replaced by equivalents without departing from the spirit and scope of the technical solutions described herein, which should fall within the scope of the appended claims.

SEQUENCE LISTING

This application contains a sequence listing which has been submitted in ASCII text file via EFS-Web and is hereby incorporated by reference in its entirety. The ASCII-formatted sequence listing, is named P1616US00 sequence listing.txt, and is 6,574 bytes in size.

SEQ ID NO: 1 in the sequence listing file is the corresponding GAPDH(H) upstream primer, and SEQ ID NO: 2 in the sequence listing file is the corresponding GAPDH(H) downstream primer;

SEQ ID NO: 3 in the sequence listing file is the corresponding Hes1(H) upstream primer, and SEQ ID NO: 4 in the sequence listing file is the corresponding Hes1(H) downstream primer;

SEQ ID NO: 5 in the sequence listing file is the corresponding Notch1(H) upstream primer, and SEQ ID NO: 6 in the sequence listing file is the corresponding Notch1(H) downstream primer;

SEQ ID NO: 7 in the sequence listing file is the corresponding Notch2(H) upstream primer, and SEQ ID NO: 8 in the sequence listing file is the corresponding Notch2(H) downstream primer;

SEQ ID NO: 9 in the sequence listing file is the corresponding VEGFR2(H) upstream primer, and SEQ ID NO: 10 in the sequence listing file is the corresponding VEGFR2(H) downstream primer;

SEQ ID NO: 11 in the sequence listing file is the corresponding p21(H) upstream primer, and SEQ ID NO: 12 in the sequence listing file is the corresponding p21(H) downstream prime;

SEQ ID NO: 13 in the sequence listing file is the corresponding MYC(H) upstream primer, and SEQ ID NO: 14 in the sequence listing file is the corresponding MYC(H) downstream primer;

SEQ ID NO: 15 in the sequence listing file is the corresponding CyclinD1(H) upstream primer, and SEQ ID NO: 16 in the sequence listing file is the corresponding CyclinD1(H) downstream primer;

SEQ ID NO: 17 in the sequence listing file is the corresponding β-catenin(H) upstream primer, and SEQ ID NO: 18 in the sequence listing file is the corresponding β-catenin(H) downstream primer;

SEQ ID NO: 19 in the sequence listing file is the corresponding FZD1(H) upstream primer, and SEQ ID NO: 20 in the sequence listing file is the corresponding FZD1(H) downstream primer;

SEQ ID NO: 21 in the sequence listing file is the corresponding KLF4(H) upstream primer, and SEQ ID NO: 22 in the sequence listing file is the corresponding KLF4(H) downstream primer;

SEQ ID NO: 23 in the sequence listing file is the corresponding GAPDH(M) upstream primer, and SEQ ID NO: 24 in the sequence listing file is the corresponding GAPDH(M) downstream primer;

SEQ ID NO: 25 in the sequence listing file is the corresponding Hes1(M) upstream primer, and SEQ ID NO:26 in the sequence listing file is the corresponding Hes1(M) downstream primer;

SEQ ID NO: 27 in the sequence listing file is the corresponding Notch1(M) upstream primer, and SEQ ID NO: 28 in the sequence listing file is the corresponding Notch1(M) downstream primer;

SEQ ID NO: 29 in the sequence listing file is the corresponding Notch2(M) upstream primer, and SEQ ID NO: 30 in the sequence listing file is the corresponding Notch2(M) downstream primer;

SEQ ID NO: 31 in the sequence listing file is the corresponding VEGFR2(M) upstream primer, and SEQ ID NO: 32 in the sequence listing file is the corresponding VEGFR2(M) downstream primer.

What is claimed is:

1. A method for improving an intestinal flora, reducing abnormally high levels of short chain fatty acids in an intestine, alleviating a colorectal inflammation, and inhibiting a colorectal cancer, wherein the method comprises administering to a subject in need thereof a composition comprising *Lactobacillus plantarum* strain CCFM164 (CGMCC 14520), and wherein the *Lactobacillus plantarum* strain CCFM164 (CGMCC 14520) has at least 90% survival rate after treatment in pH 2.5 for 3 hours.

2. The method according to claim 1, wherein *Lactobacillus plantarum* strain CCFM164 (CGMCC 14520) has at least 75% survival rate after treatment in pH 8.0 for 3 hours.

* * * * *